United States Patent
An et al.

(10) Patent No.: US 9,759,544 B2
(45) Date of Patent: Sep. 12, 2017

(54) METHODS OF REDUCING MOTION ARTIFACTS FOR OPTICAL COHERENCE TOMOGRAPHY ANGIOGRAPHY

(71) Applicants: Carl Zeiss Meditec, Inc., Dublin (CA); University of Washington through its Center for Commercialization, Seattle, WA (US)

(72) Inventors: Lin An, Walnut Creek, CA (US); Ruikang Wang, Bellevue, WA (US); Utkarsh Sharma, Dublin, CA (US)

(73) Assignees: Carl Zeiss Meditec, Inc., Dublin, CA (US); University of Washington through its Center for Commercialization, Seattle (*) Notice: Subject to any disclaimer, the term of this patent is extended or adjusted under 35 U.S.C. 154(b) by 0 days.

(21) Appl. No.: 14/821,535

(22) Filed: Aug. 7, 2015

(65) Prior Publication Data
US 2016/0040977 A1 Feb. 11, 2016

Related U.S. Application Data

(60) Provisional application No. 62/035,328, filed on Aug. 8, 2014.

(51) Int. Cl.
*G01B 11/02* (2006.01)
*G01B 9/02* (2006.01)
(Continued)

(52) U.S. Cl.
CPC ........ *G01B 9/02077* (2013.01); *A61B 3/0025* (2013.01); *A61B 3/102* (2013.01); *G01B 9/02085* (2013.01); *G01B 9/02091* (2013.01)

(58) Field of Classification Search
CPC ............ G01B 9/02077; G01B 9/02085; G01B 9/02091; A61B 3/0025; A61B 3/102
(Continued)

(56) References Cited

U.S. PATENT DOCUMENTS

| 6,549,801 B1 | 4/2003 | Chen et al. |
| 7,301,644 B2 | 11/2007 | Knighton et al. |

(Continued)

FOREIGN PATENT DOCUMENTS

WO WO 2006077107 A1 * 7/2006 ............. A61B 3/102

OTHER PUBLICATIONS

An et al., "High-Resolution Wide-Field Imaging of Retinal and Choroidal Blood Perfusion with Optical Microangiography", Journal of Biomedical Optics, vol. 15, No. 2, Mar./Apr. 2010, pp. 026011-1-026011-9.

(Continued)

*Primary Examiner* — Tarifur Chowdhury
*Assistant Examiner* — Jonathon Cook
(74) *Attorney, Agent, or Firm* — Morrison & Foerster LLP

(57) ABSTRACT

A method for reducing motion artifacts in optical coherence tomography (OCT) angiography images is disclosed. The method is applied to the intensity or complex OCT data prior to applying the motion contrast analysis and involves determining sub-pixel level shifts between at least two B-scans repeated approximately at the same location and applying the sub-pixel level shifts to the B-scans to be able to correct for motion and accurately determine motion contrast signal. A preferred embodiment includes the use of 2D cross correlations to register a series of B-scans in both the axial (z-) and lateral (x-) dimensions and a convolution approach to achieve sub-pixel level frame registration.

18 Claims, 5 Drawing Sheets

(51) Int. Cl.
*A61B 3/10* (2006.01)
*A61B 3/00* (2006.01)

(58) Field of Classification Search
USPC .................................................. 356/479, 497
See application file for complete search history.

(56) References Cited

U.S. PATENT DOCUMENTS

| | | |
|---|---|---|
| 2005/0171438 A1 | 8/2005 | Chen et al. |
| 2010/0027857 A1 | 2/2010 | Wang |
| 2011/0007957 A1* | 1/2011 | Sakagawa ............... A61B 3/102 382/131 |
| 2011/0267340 A1* | 11/2011 | Kraus .................... A61B 3/102 345/419 |
| 2012/0277579 A1 | 11/2012 | Sharma et al. |
| 2012/0307014 A1 | 12/2012 | Wang |
| 2013/0176532 A1 | 7/2013 | Sharma et al. |

OTHER PUBLICATIONS

An et al., "Using Ultrahigh Sensitive Optical Microangiography to Achieve Comprehensive Depth Resolved Microvasculature Mapping for Human Retina", Journal of Biomedical Optics, vol. 16, No. 10, Oct. 2011, pp. 106013-1106013-9.

Braff et al., "Angiography of the Retina and the Choroid with Phase-Resolved OCT using Interval-Optimized Backstitched B-Scans", Optics Express, vol. 20, No. 18, Aug. 22, 2012, pp. 20516-20534.

Elliott, F. D., Chapter 1 of "Handbook of Digital Signal Processing: Engineering Applications", Academic Press, 1987, pp. 1-53. ISBN: 0-12-237075-9.

Fingler et al., "Volumetric Microvascular Imaging of Human Retina using Optical Coherence Tomography with a Novel Motion Contrast Technique", Optics Express, vol. 17, No. 24, Nov. 19, 2009, pp. 22190-22200.

Makita et al., "Optical Coherence Angiography", Optics Express, vol. 14, No. 17, 2006, pp. 7821-7840.

Park, et al., "Real-Time Fiber-Based Multi-Functional Spectral-Domain Optical Coherence Tomography at 1.3 µm", Optics Express, vol. 13, No. 11, May 30, 2005, pp. 3931-3944.

Wang et al., "Depth-Resolved Imaging of capillary Networks in Retina and Choroid using Ultrahigh Sensitive Optical Microangiography", Optics Express, vol. 35, No. 9, May 1, 2010, pp. 1467-1469.

* cited by examiner

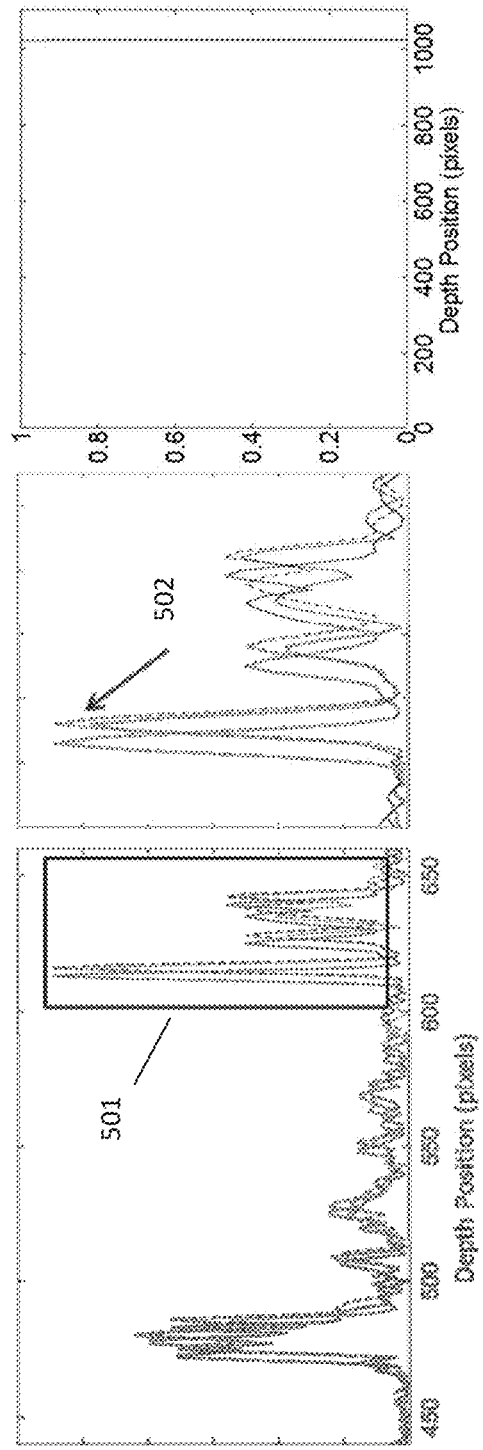

METHODS OF REDUCING MOTION ARTIFACTS FOR OPTICAL COHERENCE TOMOGRAPHY ANGIOGRAPHY

PRIORITY

The present application claims priority to U.S. Provisional Application Ser. No. 62/035,328 filed on Aug. 8, 2014, the contents of which are hereby incorporated by reference.

STATEMENT REGARDING FEDERALLY SPONSORED RESEARCH OR DEVELOPMENT

This invention was made with government support under Grant No. R01 EY024158, awarded by the National Institutes of Health. The government has certain rights in the invention.

TECHNICAL FIELD

This application relates to the field of optical coherence tomography, in particular to reduce the impact of motion artifacts in optical coherence tomography angiography imaging.

BACKGROUND

Optical coherence tomography (OCT) angiography techniques such as optical microangiography (OMAG), speckle variance, phase variance, etc. use OCT systems to achieve the imaging of functional vascular network within microcirculatory tissue beds in vivo, without the use of exogenous contrast agents. One of the major challenges of OCT angiography for in vivo imaging is the longer acquisition times and hence the associated inevitable subject movement that causes motion artifacts in the final results. Eye motion can result in image artifacts and hence greatly reduces the clinical usability of the acquired data.

US Patent Publication No. 2013/0176532, hereby incorporated by reference, describes some methods for dealing with motion artifacts in OCT Angiography data including active tracking. Previous methods that are used to reduce the motion artifacts through post-processing B-scan registration have included pixel-level shifting and phase compensation. Pixel-level accuracy shifting is an approach based on intensity OCT-structural images. This is a cross-correlation method that calculates pixel shifts in z direction between two B-scans. After determining the motion displacements (or shifts), the frames are re-registered by directly shifting the structure images without considering the phase information in the OCT signals. The limitation of this method is that it is a pixel-based approach (i.e. pixel level accuracy) and hence it could falsely register a motion contrast if there are uncompensated sub-pixel level shifts. Phase compensation uses the phase information in the OCT signals. Because the displacement (or motion) between B-scans causes the change of phase in OCT signals, the phase signal can be used to compensate motion in the spectral interferograms (or OCT signal) as discussed by Braaf et al. This method requires prior information about system parameters, such as imaging depth. Most commercial systems only provide the structural or intensity information of the OCT data and will need to be modified to obtain phase information. In addition, this method demands substantial computing power because of the repeated use of Fourier transformation operations to convert the OCT data between frequency (or wavenumber) and time (or depth structure) domain.

SUMMARY

This application describes a method to minimize/remove motion artifacts in optical coherence tomography (OCT) angiography. We describe a post-acquisition processing method that can efficiently minimize the motion artifacts due to subject movements during OCT angiography imaging of functional microvascular network within tissue beds in vivo. The invention describes a method of determining sub-pixel level shifts between B-scans repeated approximately at the same location and applying the sub-pixel level shifts to one of the B-scans to be able to accurately correct for bulk motion displacement prior to calculation of motion contrast signal. A preferred embodiment includes the use of 2D cross correlation to register a series of B-scans in both the axial (z-) and lateral (x-) dimensions and a convolution approach to achieve sub-pixel level frame registration. Compared with the existing methods, the disclosed method can realize accurate registration in real time between B-scans without the prior knowledge of system parameters (such as imaging depth, or phase-distance calibration). The method is applied to the data acquired from existing OCT based angiographic systems, meaning that it does not require any modification to the existing system set-up and data acquisition strategy.

In general, this method can be used together with any OCT based angiography processing technique (e.g. optical microangiography, speckle variance OCT, phase variance OCT, correlation mapping OCT, etc.) to improve the image quality, when imaging any part of the body using an OCT system, for example eye (both anterior and posterior chambers), skin, brain, muscle, cochlear, and internal organs if integrated with endoscope or catheter probe.

The primary advantage of this method is that it does not require prior information about the system parameters, for example imaging depth, to achieve sub-pixel accuracy for motion compensation of OCT data in subsequent frames. The method can also be applied to intensity only data and yet achieve sub-pixel level accuracy for motion compensation. The simplicity of the method allows fast processing speed, which is critical for faster analysis and review on commercial systems.

BRIEF DESCRIPTION OF THE DRAWINGS

FIG. 5(a) presents three intensity profiles extracted from three different B-scans: the reference image (dotted curve), the image to be registered (solid curve) and the image after registration (dashed curve). FIG. 5(b) shows a zoomed in view of the region marked by square 501 in FIG. 5(a). FIG. 5(c) shows the created delta function used for image registration.

FIG. 7(a) is the vasculature map produced without the disclosed motion compensation method. FIG. 7(b) is the vasculature map after using the disclosed method.

DETAILED DESCRIPTION

Figure 1:
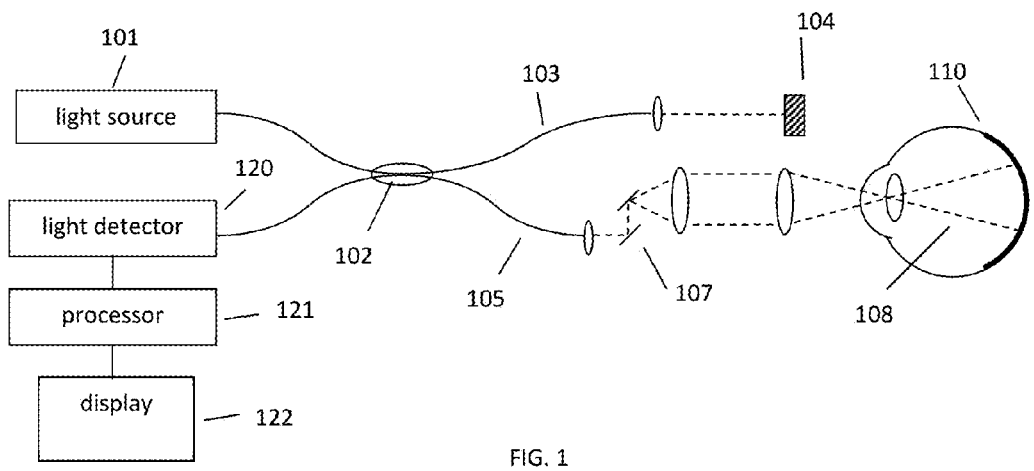
FIG. 1 is a generalized optical coherence tomography system.

A diagram of a generalized OCT system is shown in FIG. 1. Light from source 101 is routed, typically by optical fiber 105, to illuminate the sample 110, a typical sample being tissues in the human eye. The source 101 can be either a broadband light source with short temporal coherence length in the case of SD-OCT or a wavelength tunable laser source in the case of SS-OCT. The light is scanned, typically with a scanner 107 between the output of the fiber and the sample, so that the beam of light (dashed line 108) is scanned laterally (in x and y) over the area or volume to be imaged. Light scattered from the sample is collected, typically into the same fiber 105 used to route the light for sample illumination. Reference light derived from the same source 101 travels a separate path, in this case involving fiber 103 and retro-reflector 104 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 102, to form light interference in a detector 120. Although a single fiber port is shown going to the detector, those skilled in the art recognize that various designs of interferometers can be used for balanced or unbalanced detection of the interference signal. The output from the detector is supplied to a processor 121. The results can be stored in the processor 121 or displayed on display 122. The processing and storing functions may be localized within the OCT instrument or functions may be performed on an external processing unit to which the collected data is transferred. This unit could be dedicated to data processing or perform other tasks which are quite general and not dedicated to the OCT device. The processor may contain for example a field-programmable gate array (FPGA), a digital signal processor (DSP), an application specific integrated circuit (ASIC), a graphics processing unit (GPU), a system on chip (SoC) or a combination thereof, that performs some, or the entire angiography data processing steps, prior to passing on to the host processor or in a parallelized fashion.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system capable of generating data for OCT angiography analysis including spot scanning, multi-spot scanning, partial field and full field imaging systems. The techniques described herein could be applicable to any body parts, for example eye (both anterior and posterior chambers), skin, brain, muscle, cochlear, and internal organs if integrated with endoscope or catheter probe.

In Fourier Domain optical coherence tomography (FD-OCT), each measurement is the real-valued spectral interferogram ($S_j(k)$). The real-valued spectral data typically goes through several postprocessing steps including background subtraction, dispersion correction, etc. The Fourier transform of the processed interferogram, results in a complex valued OCT signal output $A_j(z)=|A_j|e^{i\Phi}$. The absolute value of this complex OCT signal, $|A_j|$, reveals the profile of scattering intensities at different path lengths, and therefore scattering as a function of depth (z-direction) in the sample. Similarly, the phase, $\phi_j$ can also be extracted from the complex valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. We use the term "cluster scan" herein to refer to a single unit or block of data generated by repeated acquisitions at the same location for the purposes of analyzing motion contrast. A cluster scan can consist of multiple A-scans or B-scans collected over time at approximately the same location(s) on the sample. A variety of ways to create B-scans are known to those skilled in the art including but not limited to along the horizontal or x-direction, along the vertical or y-direction, along the diagonal of x and y, or in a circular or spiral pattern. The majority of the examples discussed herein refer to B-scans in the x-z dimensions but the invention would apply equally to any cross sectional image.

In OCT Angiography or Functional OCT, analysis algorithms are applied to OCT data collected at the same or approximately the same sample locations on a sample at different times to analyze motion or flow (see for example US Patent Publication Nos. 2005/0171438, 2012/0307014, 2010/0027857, 2012/0277579 and U.S. Pat. No. 6,549,801 hereby incorporated by reference). Motion contrast analysis techniques can be applied to the intensity information derived from the image data, the phase information from the image data, or the complex image data. An en face vasculature image is an image displaying motion contrast signal in which the data dimension corresponding to depth is displayed as a single representative value, typically by summing or integrating all or an isolated portion of the data (see for example U.S. Pat. No. 7,301,644 hereby incorporated by reference). An example of an en face vasculature image is shown in FIG. 2.

Figure 2:
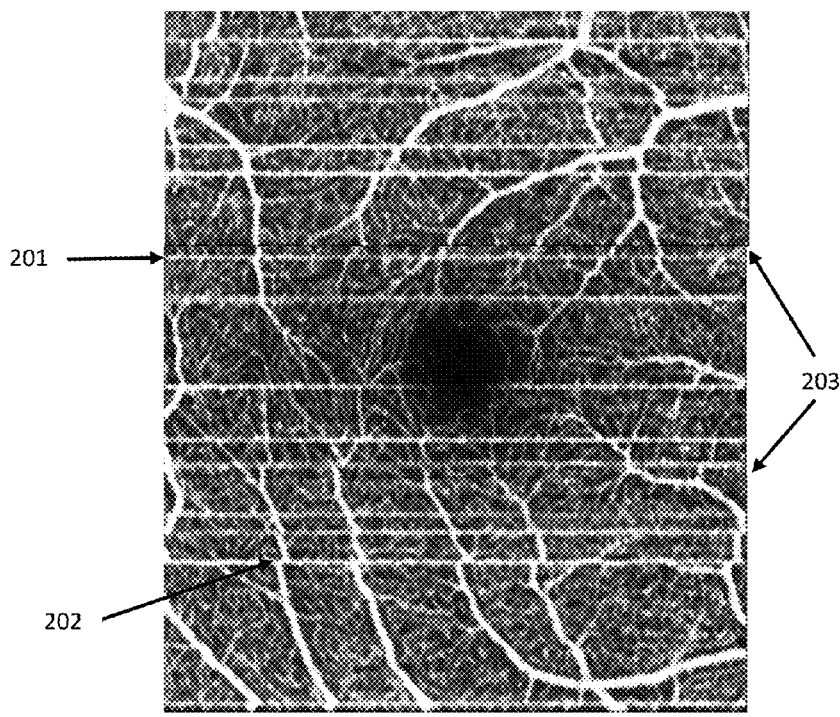
FIG. 2 shows an OCT angiography en face vasculature image with motion artifacts.

In FIG. 2, three volumes of data were collected with some overlapping area in the retina. The enface images obtained from the three volumes were montaged or combined to create a larger field of view enface image. Each B-scan in a given data volume consists of 300 A-scans, each cluster scan consists of four B-scans, and there are a total of eighty different cluster scans. Hence, the number of A-scans in a given unit data volume are 300×80×4. After processing the data to highlight motion contrast using any one of the known motion contrast techniques, a range of 50-60 pixels corresponding to 100-120 microns of tissue depth from the surface of internal limiting membrane (ILM) in retina, are summed to generate an en face image of the vasculature.

Each B-scan takes approximately 12 ms to acquire (including fly-back time) so the time between B-scans is approximately 12 ms which is on the order of interest for retinal vasculature dynamics.

For large data volume acquisitions, such as those required for motion contrast analysis as illustrated in FIG. 2, the possibility and occurrences of eye motion increases. Eye motion can result in loss of data and image artifacts, hence greatly reducing the usability of the acquired data. In the time (usually a few seconds) required to build a useful map of vasculature, the patient's gaze can shift, causing the retinal image to move from the point of view of the ophthalmic device. In the image displayed in FIG. 2, generated from data taken without any motion tracking and without any motion correction processing, there are two kinds of motion artifacts caused due to transverse eye motion that are clearly visible:

1. Horizontal line artifacts in the en face vasculature image of retina caused by small or transient transverse shifts of fixation of the eye (201)
2. Appearance of shifted blocks of data within a single cube of data caused by small changes in the fixation of the eye (202)

Figure 3:
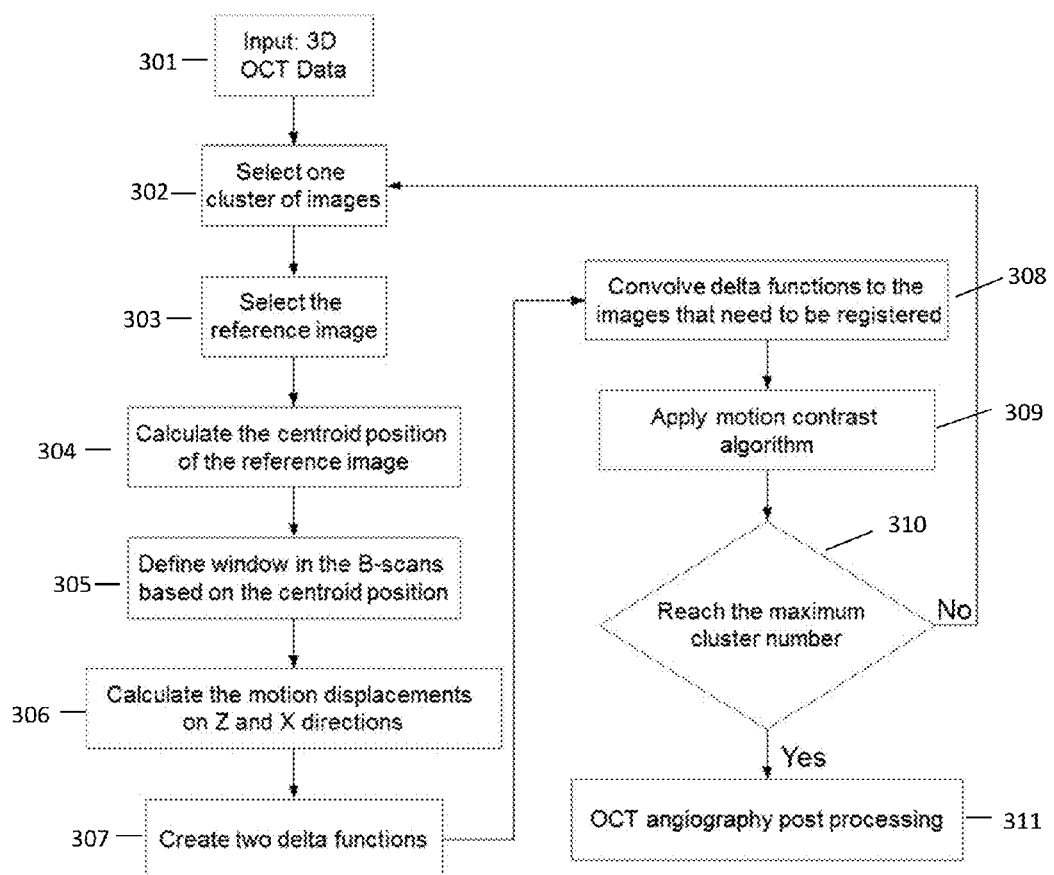
FIG. 3 shows a flow chart illustrating the steps involved with a preferred embodiment of the post-acquisition processing method.

Here we describe a post-acquisition motion correction technique to reduce the problem caused by eye motion in OCT angiography data collection. A two-phase procedure is used to correct for the bulk tissue motion in the OCT data prior to applying the motion contrast algorithm, in this case, OMAG (see for example R. K. Wang et al., "Depth-resolved imaging of capillary networks in retina and choroid using ultrahigh sensitive optical microangiography," Opt. Lett. 35(9), 1467-1469 2010 hereby incorporated by reference). The method could be applied to any type of motion contrast algorithms as is known by those skilled in the art. The two phases of the motion correction procedure are described below and illustrated in the flow chart shown in FIG. 3.

In the first phase of the method (steps 301 to 306 of the flow chart), a cross correlation method is used to calculate the relative displacements between the B-scans within a particular cluster selected (302) from a three dimensional OCT dataset (input 301), a cluster being two or more B-scans taken at approximately the same location on the sample (e.g. having greater than 80% overlap). Decreased beam overlap leads to increased background noise and hence reduced motion contrast sensitivity, especially for visualization of micro-capillary flow. This is because if the beam position is shifted by some distance, then the depth profile information of the physical structure changes between two measurements, thereby adding differential signal that is not entirely due to localized motion (see for example B. H. Park, M. C. Pierce, B. Cense, S. H. Yun, M. Mujat, G. J. Tearney, B. E. Bouma and J. F. de Boer, "Real time fiber-based multi-functional spectral-domain optical coherence tomography at 1.3 µm," Opt. Express 13, 3931 (2005)). A reference B-scan is then selected from the cluster (303). In this example, the first B-scan within each cluster is selected as a reference, but any of the B-scans could be used as the reference. To speed the cross-correlation calculation, a small window within the B-scans is selected over which to carry out the calculation. This small window is fixed at the same position across all B-scans within a cluster. Since the position of the retina (or target) changes due to subject movement, special attention is paid to the selection of the central position and the size of this small window, which should cover typical microstructure features across all B-scans. In one way to accomplish this, the centroid position of the first structure (frame) image is calculated (304). One of the approaches to determine the centroid position is to calculate an intensity weighted sum of pixels or the position index in both x and z direction. The centroid position is used to define a window in all the B-scans (305). The centroid position is designated as the central position of the window and then the window's size is chosen based on the centroid. Since the centroid calculation is intensity weighted, it is likely to be located in a region where there are sufficient pixels with high signal data, thereby containing regions of microstructural data with sufficient signal to allow determination of shifts. In a preferred embodiment, the window's width is one quarter of the whole image width and its height being approximately 600 µm (to cover the retinal thickness in the case of retinal imaging). Using the data contained in the windows of each frame, the motion displacements in the z and x dimensions are then calculated (306) as described below.

Figures 4A, 4B, 4C:
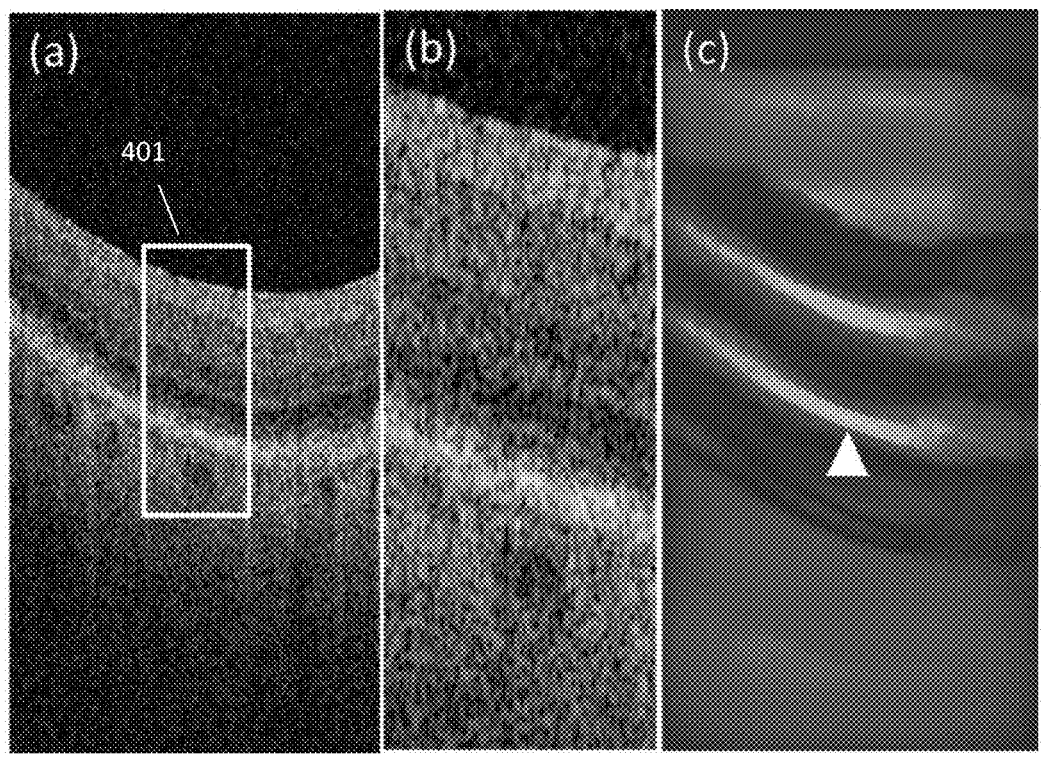
FIG. 4(a) shows a typical OCT B-scan of a retina.
FIG. 4(b) is a zoomed in view of the data contained in box 401.
FIG. 4(c) shows a cross correlation map resulting from comparing the region of the B-scan in FIG. 4(b) with another B-scan taken at approximately same location.

FIG. 4 illustrates the basic aspects of this first phase of the method. FIG. 4(a) shows a typical cross sectional microstructural image (B-scan) of a retina. Box 401 in FIG. 4 (a) is the selected small window that is used to compute the cross correlation map between the first B-scan and the rest of B-scans. The boxed area is shown in FIG. 4(b) zoomed in. The resulting cross-correlation map, comparing the first B-scan with a subsequent B-scan in the cluster, is shown in FIG. 4(c), in which the peak value position coordinates (marked by the white arrow) are used to calculate the relative displacements with respect to the first B-scan. If there was no displacement between the two B-scans, the peak value position coordinates would be precisely at the center of the cross-correlation map image (e.g. 0,0). But, if the second B-scan had some motion that resulted in relative displacements of Dz and Dx, in the z- and x-directions, then the cross-correlation map image will be able to identify the displacements as the peak value position will be shifted from the center by the amounts of Dz and Dx respectively.

Several methods can be used to ensure that sub-pixel displacement information can be extracted. It should be noted that sub-pixel implies higher resolution compared to the pixel-level resolution in the input or default B-scans. For example, if a B-scan has 1024 pixels in the z direction for a depth of 2 mm, then the pixel level accuracy for the input or default B-scan is 1.95 microns. Hence, in this case, sub-pixel level accuracy would imply that a shift in the z-direction is calculated with an accuracy greater than 1.95 microns. In one embodiment, the B-scan region selected for cross-correlation could be up-sampled prior to the cross-correlation step. In another method, the resulting cross-correlation map could be up-sampled by using a spline or other curve-fitting interpolation scheme. This will result in the determination of sub-pixel level shifts or displacement information.

It is possible to use smaller sized windows to further speed up the processing times. The reference frame could be any of the B-scans within a cluster. The cross correlation method may be applied on intensity only image data or complex image data (including both intensity and phase). Since the complex image data contains the phase information, it could achieve higher accuracy on calculating the motion displacements.

The second phase of the method (steps 307-308 of FIG. 3) is used to efficiently remove the motion artifacts among the B-scans by the use of relative displacements, Dz and Dx, calculated in the first phase to create a registered cluster of B-scans. In a preferred embodiment, to accomplish this, two delta functions are first created (307), one for the Z-direction and another one for the x-direction. The peak position of the delta function is determined by Dz and Dx. The created delta function can be written by equations (1) and (2):

$$\text{Delta}(z) = \begin{cases} \begin{cases} 1 & \text{if } z = Z - Dz \\ 0 & \text{else} \end{cases} & \text{if } Dz > 0 \\ \begin{cases} 1 & \text{if } z = -Dz \\ 0 & \text{else} \end{cases} & \text{if } Dz < 0 \text{ or } Dz = 0 \end{cases} \quad (1)$$

$$\text{Delta}(x) = \begin{cases} \begin{cases} 1 & \text{if } x = X - D \\ 0 & \text{else} \end{cases} & \text{if } Dx > 0 \\ \begin{cases} 1 & \text{if } x = -D \\ 0 & \text{else} \end{cases} & \text{if } Dx < 0 \text{ or } Dx = 0 \end{cases} \quad (2)$$

where Delta(z) and Delta(x) are the created delta functions; z and x are depth and lateral positions respectively; Z and X are the maximum depth and lateral ranges respectively; Dz and Dx are the displacements calculated in the first phase. Z, X, z and x can be represented by pixel numbers. After creating the delta functions, they are convolved with each B-scan (see for example Handbook of Digital Signal Processing: Engineering Applications by Douglas F. Elliott hereby incorporated by reference) in the cluster needing to be registered (308), resulting in the subject movement being removed/minimized within that cluster and achieving frame registration within that cluster directly in the depth structure domain.

Once the data in a particular cluster is registered, the motion contrast technique is then applied to the data in the cluster (309) to analyze the registered cluster to determine motion contrast. The overall process can be repeated for all the clusters in the OCT data set (310). After all the clusters have been processed, optional post-processing (311) can be applied to the OCT angiography data to further enhance the image quality.

FIG. 5 shows an example demonstrating the performance of the disclosed method. FIG. 5(a) shows three depth intensity profiles (A-scans) from three different B-scans: the reference B-scan (dotted line), a target B-scan from the cluster scan to be corrected (solid line), and the target B-scan after correction (dashed line). Box 501 highlights a selected window of the data in FIG. 5(a). FIG. 5(b) shows a zoomed in view of the data contained in Box 501 to better illustrate the differences between the three profiles. As shown in both FIGS. 5(a) and 5(b), due to the movement, the solid curve is shifted to the right side compared to the dotted curve. Using Equation (1), a delta function is created, which is shown in FIG. 5(c). Convolving the delta function with the solid curve results in a corrected A-scan, shown in FIGS. 5(a) and 5(b) as a dashed line. As evident from FIG. 5(b), the highest peaks (pointed by black arrow 502) of the reference A-scan and corrected A-scan are registered with each other, indicating that the displacement caused by the motion has been compensated.

Figures 6A, 6B:
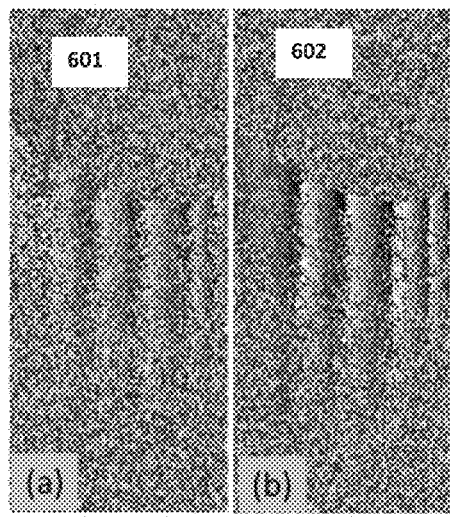
FIG. 6(a) shows the phase difference map between two B scans in a cluster scan before applying the motion correction compensation described herein.
FIG. 6(b) is the phase difference map between the B-scans after applying the disclosed motion compensation method

FIG. 6 shows phase difference maps calculated between two B-scans in a cluster scans, which can be used to indicate relative movement between them. FIG. 6(a) is the phase difference map between two B scans before applying the motion correction compensation described herein. FIG. 6(b) is the phase difference map between the B-scans after applying the disclosed method.

Before compensation, the phase noise is high (e.g. at the position pointed by arrow 601 in FIG. 6(a)), which indicates the correlation between two frames is low. After applying the disclosed method, the phase noise is significantly reduced as seen in FIG. 6(b). Compared to FIG. 6(a), the phase noise is much lower (e.g. at the position pointed by arrow 602 in FIG. 6(b)).

Figures 7A, 7B:
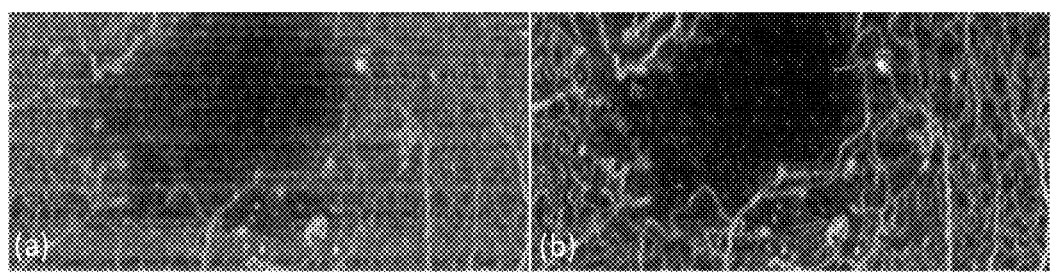
FIGS. 7(a) and 7(b) presents two retina vasculature en face projection maps captured from a diabetic retinopathy patient.

FIG. 7 presents two retina vasculature en face projection maps captured from a diabetic retinopathy patient in which OCT data was processed using OMAG that further demonstrate the performance of the motion compensation method as disclosed here. In this example, a 27 kHz ZEISS Cirrus-4000 HD-OCT system was used to acquire image data from a subject having diabetic retinopathy. In generating the enface images, the number of B scans in the cluster was 4. Each B-scan was comprised of 300 A-scans (corresponding to ~3 mm in distance). There were 80 spatial locations in the slow axis where the clusters of B-scans were captured, covering ~1 mm in distance. The enface images were produced by taking the maximum projection of the OMAG signal along the depth direction. The enface image has a field of view of ~3×1.2 mm$^2$. FIG. 7(a) is the vasculature map produced without the disclosed motion compensation method. FIG. 7(b) is the vasculature map after using the disclosed method. Compared to FIG. 7(a), the image quality of FIG. 7(b) was improved significantly. The obvious horizontal line pattern artifacts in FIG. 7(a) (caused by the eye motion) are removed in FIG. 7(b), and the contrast for retinal vasculatures is greatly enhanced. Some typical retinal diabetic symptoms, such as micro-aneurysms (pointed by the arrows), are clearly demonstrated in FIG. 7(b).

In a further embodiment, intensity or complex data B-scans could be up-sampled in both x and z prior to the registration step. The process of up-sampling provides an image with higher pixel density. Applying the motion correction processing steps on the higher pixel density data or images could further improve the accuracy of the calculated shifts, thereby providing sub-pixel level accuracy. One example of up-sampling is to use a zero-padding approach in the spectral domain of the captured OCT spectral data, and employ Fourier transformation to up-sample the intensity B-scan images. Once the subsequent up-sampled frames have been registered, improved accuracy motion contrast can be calculated. The OCT data could be down-sampled either before or after calculating the motion contrast signal. In another embodiment, the sampling frequency in either x or z or both dimension could be equal to or greater than the Nyquist spatial frequency limits in x and z respectively.

The basic concept disclosed herein may also be extended for 3D motion correction. As the speeds of OCT systems increase, it may be possible to repeat several 3D OCT data collection steps at approximately the same location. The two 3D OCT volume data sets can be compared and hence, in addition to x and z, y shifts can also be determined and corrected for. For example, in one embodiment, enface OCT image data from the two 3D data sets could be used to find out shifts in x and y (Dx and Dy) and the displacement information could be applied to correct one of the 3D data sets prior to motion contrast generation.

Portions of the methods described herein or their various steps may represent a module, a segment, or a portion of program code, which includes one or more instructions executable by a processor for implementing specific logical functions or steps in the process. The program code may be stored on any type of computer readable medium, for example, such as a storage device including a disk or hard drive. The physical computer readable storage medium comprises instructions executable to perform functions to reduce the impact of motion on OCT Angiography data. The computer readable medium may include a physical and/or non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, a tangible storage device, or other article of manufacture, for example. Alternatively, program code, instructions, and/or data structures may be transmitted via a communications network via a propagated signal on a propagation medium (e.g., electromagnetic wave(s), sound wave(s), etc.).

The following references are hereby incorporated by reference:

PATENT REFERENCES

US Patent Publication No. 2005/0171438
US Patent Publication No. 2012/0307014
US Patent Publication No. 2010/0027857
US Patent Publication No. 2012/0277579
US Patent Publication No. 2013/0176532
U.S. Pat. No. 6,549,801
U.S. Pat. No. 7,301,644

NON-PATENT LITERATURE

Shuichi Makita, Youngjoo Hong, Masahiro Yamanari, Toyohiko Yatagai, and Yoshiaki Yasuno, Optical coherence angiography, Optics Express, Vol. 14, Issue 17 7821, 2006.

Boy Braaf, Koenraad A. Vermeer, Kari V. Vienola, and Johannes F. de Boer, Angiography of the retina and the choroid with phase-resolved OCT using interval-optimized backstitched B-scans, Optics Express, Vol. 20, No. 18 20516-20534, 2012.

Fingler, R. J. Zawadzki, J. S. Werner, D. Schwartz, and S. E. Fraser, "Volumetric microvascular imaging of human retina using optical coherence tomography with a novel motion contrast technique," Opt. Express 17(24), 22190-22200 (2009).

R. K. Wang, L. An, P. Francis, and D. J. Wilson, "Depth-resolved imaging of capillary networks in retina and choroid using ultrahigh sensitive optical microangiography," Opt. Lett. 35(9), 1467-1469 (2010).

B. H. Park, M. C. Pierce, B. Cense, S. H. Yun, M. Mujat, G. J. Tearney, B. E. Bouma and J. F. de Boer, "Real time fiber-based multi-functional spectral-domain optical coherence tomography at 1.3 µm," Opt. Express 13, 3931 (2005).

What is claimed is:

1. A method to reduce the effects of motion in functional optical coherence tomography (OCT) imaging of a sample, said method comprising:
collecting a cluster of OCT B-scans of the sample with an OCT system, said cluster containing at least two B-scans, wherein at least two B-scans have an overlap of greater than 80%;
calculating displacements in two dimensions between the B-scans in the cluster;
registering the B-scans in the cluster using the calculated displacements;
analyzing the registered cluster to obtain functional information of the sample; and
storing or displaying the functional information.

2. A method as recited in claim 1, in which the sample is a human eye.

3. A method as recited in claim 1, in which the analyzing step includes applying an optical microangiography (OMAG) technique to the registered cluster.

4. A method as recited in claim 1, in which the registering step is carried out in the depth structure domain.

5. A method as recited in claim 1, in which the displacements are calculated on intensity B-scan data.

6. A method as recited in claim 1, in which the displacements are calculated on complex B-scan data.

7. A method as recited in claim 1, in which the calculating step is performed by taking cross-correlations between sub-regions of the B-scans in the cluster.

8. A method as recited in claim 1, in which the registering step involves creating delta functions from the displacements and convolving the delta functions to the B-scans to be registered.

9. A method as recited in claim 1, in which upsampling is used in the calculating step to improve the accuracy of the calculated displacements.

10. A non-transitory computer-readable medium storing a program which upon execution by a computer causes the computer to execute each step of an analysis method of an optical coherence tomography system said method comprising:
calculating displacements in two dimensions between a plurality of B-scans in a cluster of B-scans collected with an optical coherence tomography system and wherein at least two B-scans have an overlap of greater than 80%;
registering the B-scans in the cluster using the calculated displacements;
analyzing the registered cluster to obtain functional information of the sample; and
storing or displaying the functional information.

11. A non-transitory computer-readable medium as recited in claim 10, in which the sample is a human eye.

12. A non-transitory computer-readable medium as recited in claim 10 in which the analyzing step includes applying an optical microangiography (OMAG) technique to the registered cluster.

13. A non-transitory computer-readable medium as recited in claim 10, in which the registering step is carried out in the depth structure domain.

14. A non-transitory computer-readable medium as recited in claim 10, in which the displacements are calculated on intensity B-scan data.

15. A non-transitory computer-readable medium as recited in claim 10, in which the displacements are calculated on complex B-scan data.

16. A non-transitory computer-readable medium as recited in claim 10, in which the calculating step is performed by taking cross-correlations between sub-regions of the B-scans in the cluster.

17. A non-transitory computer-readable medium as recited in claim 10, in which the registering step involves creating delta functions from the displacements and convolving the delta functions to the B-scans to be registered.

18. A non-transitory computer-readable medium as recited in claim 10, in which upsampling is used in the calculating step to improve the accuracy of the calculated displacements.

* * * * *

UNITED STATES PATENT AND TRADEMARK OFFICE
CERTIFICATE OF CORRECTION

PATENT NO. : 9,759,544 B2  
APPLICATION NO. : 14/821535  
DATED : September 12, 2017  
INVENTOR(S) : Lin An et al.

Page 1 of 1

It is certified that error appears in the above-identified patent and that said Letters Patent is hereby corrected as shown below:

In the Specification

In Column 3, Line 5, after "method" insert -- . --.

In Column 5, Line 20, after "(201)" insert -- . --.

In Column 5, Line 23, after "(202)" insert -- . --.

Signed and Sealed this  
First Day of May, 2018

Andrei Iancu  
*Director of the United States Patent and Trademark Office*